Jan. 15, 1957 E. S. BOERNER Plant Pat. 1,555
CHRYSANTHEMUM PLANT
Filed Feb. 27, 1956
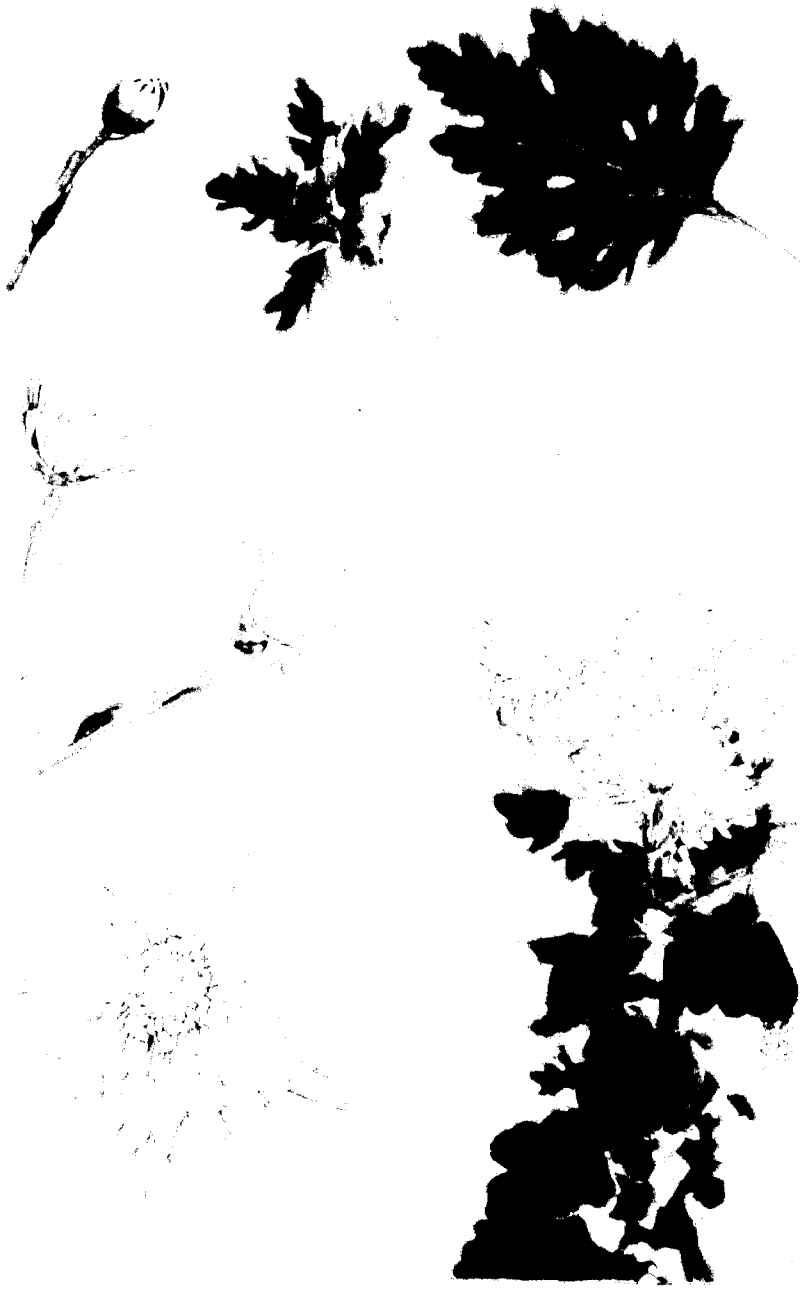
Inventor.
E. S. Boerner
By: Robb & Robb
Attorneys.

United States Patent Office

Plant Pat. 1,555
Patented Jan. 15, 1957

1,555

CHRYSANTHEMUM PLANT

Eugene S. Boerner, Newark, N. Y., assignor to Jackson & Perkins Company, Newark, N. Y., a corporation of New York Application February 27, 1956, Serial No. 568,132

1 Claim. (Cl. 47—60)

The present invention relates to a new and distinct variety of chrysanthemum plant of the decorative type, which was originated by me by crossing the variety "Wood Duck" (Plant Patent No. 1,310) with the variety "Lavender Lady" (unpatented).

The primary objective of this breeding was to produce a new chrysanthemum variety which embodies the beauty of the plant and flower of the parent variety "Wood Duck," but which combines therewith the flower color of the parent variety "Lavender Lady," as well as an earlier-flowering chrysanthemum in the "Lavender Lady" color. This objective was fully achieved, along with other improvements and advantages, as evidenced by the fact that the new variety is characterized by the attractiveness of its plant and flowers; the earliness of its bloom; the large size of its flowers; the long persistence of its blooming habit until after the first frosts, which is an especially desirable and valuable characteristic; and the distinctive Pale Rhodonite Pink, lightly overcast with Rose Pink, general color tonality of its flowers.

The foregoing characteristics definitely differentiate the new variety from its parents, as well as from all other varieties of its class of which I am aware, and asexual reproduction of the new variety by both top cuttings and underground runners, as performed by me at Newark, New York, shows that these characteristics and distinctions come true to form and are established and transmitted through succeeding propagations.

The accompanying drawing shows typical specimens of the vegetative growth and flowers of my new variety in different stages of development, as well as a typical specimen plant, all as depicted in color as nearly true as it is reasonably possible to make the same in a color illustration of this character.

The following is a detailed description of my new variety, with color terminology in accordance with Ridgway's Color Standards and Nomenclature:

Parentage: "Wood Duck" × "Lavender Lady."
Classification: Decorative type.
Growth: From 20 inches to 24 inches tall.
Cold resistance: Winter hardy in northern New York; flowers show no frost burn with early frosts, as compared with other varieties grown under comparable cultural conditions in northern New York.
Blooming period: In northern New York climatic area, blooming begins about September 20th and continues until heavy frosts.

FLOWER (Observations made from specimens grown in a field at Newark, New York, in early October, and near mid-afternoon.)

Bud:
- *Color.*—When sepals first divide—Pale Rhodonite Pink, Plate 38. When petals begin to unfurl—Pale Amaranth Pink, Plate 12. When half-blown: Inside of petals—Rosolane Pink, Plate 26, lightly overcast with Pale Rose-Purple, Plate 26; outside of petals—Pale Rhodonite Pink, Plate 38, lightly overcast with Rosolane Pink, Plate 26.
- *Peduncle.*—Strong. Color—Light Cress Green, Plate 31.

Bloom:
- *Size.*—From 4½ inches to 5 inches.
- *Stem.*—Strong.
- *Form.*—Decorative type.
- *Petalage.*—Double.
- *Color.*—Center of flower—Rose Pink, Plate 12. Outer petals—Pale Rhodonite Pink, Plate 38. Base of petals—Deep Sea-foam Green, Plate 31. Inside of petals—Pale Rhodonite Pink, Plate 38, lightly overcast with Rose Pink, Plate 12. Reverse of petals—White, Plate 53, lightly overcast with Pale Rhodonite Pink, Plate 38.
- *Petals.*—Texture—stiff. Form—oval.
- *Fragrance.*—Characteristic chrysanthemum.

PLANT

Form: Compact; bushy.
Growth: Free.
Foliage:
- *Size.*—Medium.
- *Quantity.*—Normal.
- *Color.*—Upper side—Dark Dull Yellow-Green, Plate 32; reverse side—Elm Green, Plate 17.
- *Texture.*—Leathery.

I claim:

A new and distinct variety of chrysanthemum plant of the decorative type, substantially as herein shown and described, characterized particularly as to novelty by the attractiveness of its plant and flowers, the earliness of its bloom, the large size of its flowers, the long persistence of its blooms until after the first frosts, and the distinctive Pale Rhodonite Pink, lightly overcast with Rose Pink, general color tonality of its flowers.

No references cited.